United States Patent [19]

Mougin et al.

[11] Patent Number: 5,753,215
[45] Date of Patent: May 19, 1998

[54] COSMETIC COMPOSITION CONTAINING A PSEUDO-LATEX HAVING REMANENCE PROPERTIES

[75] Inventors: Nathalie Mougin, Paris; Jean Mondet, Drancy; Monique Guelton, Saint Maur; Bertrand Piot, La Garenne-Colombes; Christine Dupuis; Daniele Cauwet, both of Paris, all of France

[73] Assignee: L'Oreal, Paris, France

[21] Appl. No.: 613,604

[22] Filed: Mar. 11, 1996

Related U.S. Application Data

[63] Continuation of Ser. No. 257,624, Jun. 8, 1994, abandoned.

[30] Foreign Application Priority Data

Jun. 8, 1993 [FR] France ................... 93 06827

[51] Int. Cl.$^6$ ................. A61K 7/11; A61K 7/48
[52] U.S. Cl. ............... 424/70.11; 424/70.15; 424/401; 424/62; 424/70.7
[58] Field of Search .............. 424/70.11–70.17, 424/401, 47, 62, 63, 64

[56] References Cited

U.S. PATENT DOCUMENTS

| | | | |
|---|---|---|---|
| 3,850,178 | 11/1974 | Schoenholz | 132/7 |
| 3,927,199 | 12/1975 | Micchelli | 424/70.17 |
| 4,710,374 | 12/1987 | Grollier | 424/70.16 |
| 4,859,455 | 8/1989 | Nowak | 424/70.16 |
| 4,960,814 | 10/1990 | Wu et al. | 524/132 |
| 4,985,239 | 1/1991 | Yahagi | 424/70.16 |
| 5,120,531 | 6/1992 | Wells | 424/70.16 |

FOREIGN PATENT DOCUMENTS

| | | |
|---|---|---|
| 0138395 | 4/1985 | European Pat. Off. . |
| 0214626 | 3/1987 | European Pat. Off. . |
| 0370764 | 5/1990 | European Pat. Off. . |
| 0418676 | 3/1991 | European Pat. Off. . |
| 0539251 | 4/1993 | European Pat. Off. . |
| 1049063 | 11/1966 | United Kingdom . |
| 2034724 | 6/1980 | United Kingdom . |
| 2148714 | 6/1985 | United Kingdom . |
| 8912438 | 12/1989 | WIPO . |

OTHER PUBLICATIONS

H. Ibrahim et al., "Concept and development of ophthalmic pseudo-latexes triggered by pH", International Journal of Pharmaceutics, vol. 77, No. 2,3, Nov. 15, 1991, pp. 211–219.
Chemical Abstracts, vol. 97, No. 18, Nov. 1982, Abstract No. 150584k, p. 382.

*Primary Examiner*—Sally Gardner-Lane
*Attorney, Agent, or Firm*—Oliff & Berridge, PLC

[57] ABSTRACT

Cosmetic composition for topical or hair application.

This composition contains, in a suitable cosmetic vehicle, a pseudo-latex consisting of particles of a film-forming radical polymer containing carboxylic acid functions, neutralized to a degree of neutralization between 10 and 80% using a polyfunctional neutralizing agent consisting either of a diamine or of the combination of a polyvalent metal salt and an inorganic or organic base, the average diameter of the said particles being between 10 and 450 nm.

The composition preferably takes the form of a shampoo, a conditioner, a styling or treating lotion or gel or a hair shaping product, or the form of a make-up product such as a mascara or a nail varnish.

16 Claims, No Drawings

COSMETIC COMPOSITION CONTAINING A PSEUDO-LATEX HAVING REMANENCE PROPERTIES

This is a Continuation of application Ser. No. 08/257,62 filed Jun. 8, 1994, now abandoned.

The subject of the present invention is a cosmetic composition intended for topical or hair application containing a pseudo-latex.

More particularly, the subject of the present invention is cosmetic compositions in the form of shampoo, conditioner, a styling or treating lotion or gel or a hair shaping product, or alternatively in the form of a make-up product such as a mascara or a nail varnish.

It is common practice in numerous cosmetic formulations to use a variable proportion, depending on the nature of the formulation, of at least one film-forming substance which makes it possible, on the one hand, to impart more hold and softness to hair and, on the other hand, a harder and more shiny film to nails, which adheres perfectly to the nails. The film-forming substance ought, however, to have a good affinity for the keratin of hair and nails.

In other terms, once the composition has been applied, the film-forming substance should display remanence properties, that is to say be difficult to remove from its support by a simple washing with water or using a shampoo.

After various studies on a very great number of film-forming polymers, it has just now been observed that it was possible to obtain excellent remanence properties in various cosmetic compostions by using pseudo-latexes.

As is well known, and as will be used hereinafter, the expression "pseudo-latex" denotes a suspension consisting of generally spherical particles of a polymer, these being obtained by dispersion of the polymer in a suitable aqueuous phase.

The expression "pseudo-latex" should not be confused with the expression "latex" or "synthetic latex" which is also a suspension consisting of particles of a polymer which are obtained directly by polymerization of one or more monomers in a suitable aqueous phase.

The subject of the present invention as novel industrial product is a cosmetic composition intended for topical or hair application, this composition containing, in a suitable cosmetic vehicle, a pseudo-latex consisting of particles of a film-forming radical polymer containing carboxylic acid functions neutralized to a degree of neutralization between 10 and 80% using a polyfunctional neutralizing agent consisting either of a diamine or of the combination of a polyvalent metal salt and an organic or inorganic base, the average diameter of the said particles being between 10 and 450 nm.

The film-forming radical polymers of the pseudo-latex, containing carboxylic acid functions, are obtained from unsaturated monomers by radical reaction and preferably have an average molecular weight between 1,000 and $10^6$ measured, for example by steric exclusion chromatography.

These polymers are water-insoluble and essentially are film-forming radical polymers commonly used for the preparation of cosmetic compositions.

Among these film-forming radical polymers containing carboxylic acid functions there may in particular be mentioned:

- the polyoxyethylenated vinyl acetate/crotonic acid copolymer sold by the company Hoechst under the name "Aristoflex A", of acid number 56,

- the vinyl acetate/crotonic acid (90/10) copolymer sold by the company BASF under the name "Luviset CA66", of acid number 74,

- the vinyl acetate/crotonic acid/vinyl neodecanoate terpolymer sold by the company National Starch under the name "Resin 28-29-30", of acid number 65,

- the N-octylacrylamide/methyl methacrylate/ hydroxypropyl methacrylate/acrylic acid/tert-butylaminoethyl methacrylate copolymer sold by the company National Starch under the name "Amphomer", of acid number 137,

- the alternating methyl vinyl ether/maleic anhydride (50/50) copolymer monoesterified with butanol sold by the company GAF under the name "Gantrez ES 425", of acid number 260,

- the acrylic acid/ethyl acrylate/N-tert-butyl-acrylamide terpolymer sold by the company BASF under the name "Ultrahold 8", of acid number 62.

It is also possible, according to the invention, to use other types of film-forming polymers containing carboxylic acid functions, such as those described in French Patent No. 78 30596 (2,439,798) having the following general formula:

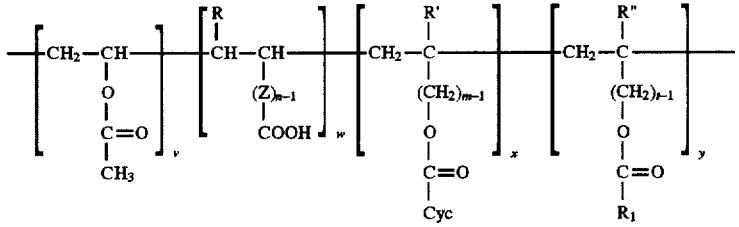

in which:

R, R' and R", which may be identical or different, represent a hydrogen atom or a methyl radical, m, n and t are 1 or 2, $R_1$ represents a saturated or unsaturated linear or branched alkyl radical having from 2 to 21 carbon atoms, Z represents a divalent radical taken from the group consisting of: —$CH_2$—, —$CH_2$—O—$CH_2$— and —$CH_2$—O—$(CH_2)_2$—, Cyc represents a radical chosen from:

(i) a radical of formula:

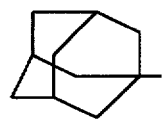

(ii) a radical of formula:

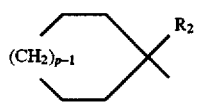

in which:

R₂ represents a hydrogen atom or a methyl radical, and p is 1 or 2.

(iii) a radical of formula:

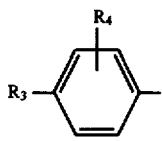

in which:

R₃ represents a hydrogen atom or a methyl, ethyl, tert-butyl, ethoxy, butoxy or dodecyloxy radical and R₄ represents a hydrogen atom, an alkyl radical of 1 to 4 carbon atoms or an alkoxy radical of 1 to 4 carbon atoms, and (iv) a radical of formula:

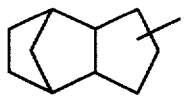

v represents from 10 to 91% and preferably from 36 to 84% by weight, w represents from 3 to 20% and preferably from 6 to 12% by weight, x represents from 4 to 60% and preferably from 6 to 40% by weight, and y represents from 0 to 40% and preferably from 4 to 30% by weight, v+w+x+y being equal to 100%.

The pseudo-latex of the cosmetic positions according to the invention is obtained according to the known methods for the preparation of pseudo-latexes, subject, however, to certain particular features which will be mentioned below.

The general process for the preparation of pseudo-latexes consists in dissolving a water-insoluble polymer in an organic solvent which is soluble or partially soluble in water, in dispersing the solution thus obtained in water with stirring and in subsequently removing the organic solvent by evaporation under vacuum, which leads to a suspension consisting of particles of the polymer, the size of which particles is generally less than 1 µm.

According to this general process, the use of a surfactant, of a mixture of surfactants or of a protective colloidal polymer or alternatively of a surfactant/protective colloidal polymer mixture is essential, with a view to obtaining good stabilization of the particles.

As mentioned above, the film-forming radical polymers containing carboxylic acid functions as defined above must be neutralized in order to prepare pseudo-latexes with a degree of neutralization lower than 100%, with a view to avoiding their total solubilization in water.

Upon partial neutralization of the polymers, the pseudo-latexes obtained are particularly stable in the absence of hydrophilic stabilizer or of surfactant or alternatively of protective colloid.

The degree of neutralization of the film-forming polymers containing carboxylic acid functions should thus be determined perfectly, such that they remain water-insoluble while being soluble in the organic solvent.

It goes without saying that the degree of neutralization upper limit which ought not to be exceeded for the polymer to remain water-insoluble will depend upon the nature of each film-forming polymer containing carboxylic acid functions and on the neutralizing agent. Generally, when the neutralizing agent is a diamine, the degree of neutralization is generally between 30 and 80% and preferably between 40 and 70% if the polymer contains less than 2 meq/g of carboxylic acid functions and between 10 and 50%, preferably between 10 and 40%, if the polymer contains more than 2 meq/g of carboxylic functions.

When the polyfunctional neutralizing agent consists of the combination of a polyvalent metal salt and an inorganic or organic base, the polymer is first of all neutralized to a degree between 4 and 20%, and preferably between 4 and 10%, by the polyvalent metal salt and is then co-neutralized with the inorganic or organic base to a total degree of neutralization between 30 and 80%, preferably between 40 and 70%, if the polymer contains less than 2 meq/g of carboxylic acid functions and between 10 and 50%, preferably between 10 and 40%, if the polymer contains more than 2 meq/g of carboxylic acid functions.

According to the invention, the diamines as neutralizing agents are chosen from lysine, arginine or cystine. The polyvalent metal salts are chosen from the bromides, chlorides, nitrates, acetates, carbonates and sulphates of calcium, zinc, magnesium, barium, aluminium and zirconium.

The inorganic or organic bases used as co-neutralizing agents with the polyvalent metal salts are chosen, for example, from sodium hydroxide, potassium hydroxide or aqueous ammonia or from an amino alcohol chosen from 2-amino-2-methyl-1-propanol (AMP), triethanolamine, triisopropanolamine (TIPA), monoethanolamine, diethanolamine, tri[1-(2-hydroxy)propyl]amine, 2-amino-2-methyl-1,3-propanediol (AMPD) and 2-amino-2-hydroxymethyl-1,3-propanediol.

The co-neutralizing agent may, of course, also be a diamine such as mentioned above.

The process for the preparation of the pseudo-latex used according to the invention depends upon the nature of the polyfunctional neutralizing agent.

When the neutralizing agent is a diamine such as lysine, neutralization of the carboxylic acid functions of the film-forming polymer is performed either in situ in the solution of the polymer in the organic solvent, by adding the determined amount of the diamine, or during the preparation of the emulsion, the neutralizing agent then being in the aqueous phase of the emulsion. The organic solvent used should be a volatile solvent or a mixture of such solvents having a boiling point lower than that of water and be miscible or partially miscible with water.

The organic solvent as defined above is preferably chosen from acetone, methyl ethyl ketone, tetrahydrofuran, methyl acetate, ethyl acetate, isopropanol and ethanol.

After production of the solution of the partially neutralized polymer in the organic solvent, an emulsion is then prepared by pouring with stirring, into the organic solution obtained, a suitable amount of water optionally containing an anti-foaming agent the role of which will be to facilitate the subsequent evaporation of the organic phase.

According to one variant of the process as defined above, neutralization of the carboxylic acid functions of the polymer dissolved in the organic solvent may be performed during the formation of the emulsion by pouring into it an aqueous solution containing the required amount of the diamine.

During the formation of the emulsion the stirring is preferably performed using a shearing disperser of the Moritz or Ultra-Turrax or Raineri type fitted with deflocculant blades.

The emulsion thus obtained is particularly stable without it being necessary to use a surface-active agent, in so far as the carboxylate groups of the polymer position themselves at the interface with the water and protect the droplets from coalescence by electrostatic repulsion.

After formation of the emulsion at a temperature between room temperature and approximately 70° C., the evaporation of the organic solvent is then performed under reduced pressure until it is totally removed, the evaporation preferably being carried out with gentle heating.

A pseudo-latex is thus obtained, that is to say an aqueous dispersion of particles of the film-forming polymer, which is free from any surfactant or other hydrophilic stabilizing agent while being very stable.

When the polyfunctional neutralizing agent consists of the combination of a polyvalent metal salt and an inorganic or organic base, the process for the preparation of the pseudo-latex is performed in two steps under similar operating conditions. In a first step, partial neutralization of the carboxylic acid functions of the polymer is performed in an organic solvent medium using the polyvalent metal salt and, in a second step, the base acting as co-neutralizing agent is then added with a view to obtaining a dispersion. In fact, neutralization of the polymer by the base and then by the polyvalent metal salt does not make it possible to obtain a dispersion, but results in decantation of the polymer.

According to a preferred embodiment, the polyvalent metal salt is a zinc salt and preferably zinc acetate.

The use according to the invention of polyfunctional neutralizing agents allows interactions between the polymer chains, leading to the formation of a cross-linked network during the formation of the film, which explains the greater insolubility with respect to water, shampoos and detergents.

The average size of the particles of the pseudo-latexes is preferably between 20 and 430 nm.

The particle size polydispersity is relatively small according to this process for the preparation of the pseudo-latex, and when measured by quasielastic light scattering is generally between 0.1 and 0.40 and preferably lower than 0.35.

During the preparation, a plasticizing agent may be introduced into the solution of the organic solvent in a proportion between 5 and 40% and preferably between 10 and 30% by weight relative to the weight of the non-neutralized film-forming polymer, and this with a view to improving the cosmetic and mechanical properties, it being possible for this plasticizer to be hydrophilic or hydrophobic. Among the hydrophilic plasticizers there may be mentioned glycol ethers and in particular:

Carbitols from the company Union Carbide, namely Carbitol or diethylene glycol ethyl ether, methyl Carbitol or diethylene glycol methyl ether, butyl Carbitol or diethylene glycol butyl ether or alternatively hexyl Carbitol or diethylene glycol hexyl ether, Cellosolves from the company Union Carbide, namely Cellosolve or ethylene glycol ethyl ether, butyl Cellosolve or ethylene glycol butyl ether, hexyl Cellosolve or ethylene glycol hexyl ether, Dowanols from the company Dow Chemical and in particular Dowanol PM or propylene glycol methyl ether, Dowanol DPM or dipropylene glycol methyl ether, Dowanol TPM or tripropylene glycol methyl ether or alternatively Dowanol DM or diethylene glycol methyl ether.

There may also be mentioned as other hydrophilic plasticizing agents:

oxyethylenated castor oil containing 40 moles of ethylene oxide such as that sold under the name "Mulgofen EL-719" by the company Rhôfiê Poulenc, benzyl alcohol, triethyl citrate sold by the company Pfizer under the name "Citroflex-2", 1,3-butylene glycol, propylene carbonate, lauric acid diethanolamide sold by the company Mona Industries under the name "Monamid 716", diethyl tartrate, diethyl phosphate, and glycerol diacetate (diacetin).

Among these various hydrophilic plasticizing agents it is preferred to use the Dowanols from the company Dow Chemical in the preparation of the pseudo-latexes.

Among the hydrophobic plasticizing agents there may be mentioned:

diethyl, dibutyl and di-2-ethylhexyl phthalates and adipates, dibutyl tartrate, dibutyl and di-2-ethyhexyl phosphates, derivatives of propylene glycol chosen from: propylene glycol phenyl ether, propylene glycol diacetate, dipropylene glycol butyl ether and tripropylene glycol butyl ether, glycerol esters such as glycerol triacetate (triacetin).

The concentration by weight of the film-forming polymer in the form of particles in the pseudo-latex obtained by the process as described above is generally between 5 and 50% and preferably between 10 and 25% relative to the total weight of the pseudo-latex.

The viscosity of the pseudo-latexes at a concentration of 25% by weight of film-forming polymer particles should preferably be between 10 and $3,000 \times 10^{-3}$ Pa.s (10 cp and 3000 cp) (measured on a Contraves machine at 25° C.).

The cosmetic compositions according to the invention generally have a pH approximately between 7 and 7.2.

As mentioned above, the cosmetic compositions according to the invention may take various forms, for example shampoos, conditioners, lotions or gels for blow-drying or hair setting, permanent wave or hair straightening compositions, dyeing or bleaching compositions. The compositions according to the invention may also take the form of make-up products for the eyelashes and nails such as mascaras or nail varnishes. The compositions according to the invention may in addition take the form of nail care products, optionally containing active principles and in particular of water-soluble type such as moisturizing agents and/or hardeners, as well as in the form of pre-coating compositions for nails with a view to subsequent application of a nail varnish, it being also possible for these pre-coating compositions to contain active principles which are water-soluble or dispersed in the composition.

The proportion by weight of the polymer particles in these compositions is between 0.5 and 30% relative to the total weight of the composition, and preferably between 1 and 15%.

The compositions of the invention may contain UV-A or UV-B or broadband sunscreen agents and be used as anti-sun products.

They may also take the form of deodorants or of compositions for oral use such as mouthwashes or toothpastes.

The compositions according to the invention may contain conventional cosmetic adjuvants chosen from fatty substances, organic solvents, silicones, thickening agents, emollients, UV-A or UV-B or broadband sunscreen agents, anti-foaming agents, moisturizing agents, humidifying agents, anionic, nonionic or amphoteric polymers or their mixtures, anti-perspirants, basifying agents, dyes, pigments and propellants when the compositions take the form of an aerosol.

There may more precisely be used as fatty substance an oil or a wax or mixture thereof, fatty acids, fatty alcohols, fatty acid esters such as $C_6$ to $C_{18}$ fatty acid triglycerides, petroleum jelly, paraffin, lanolin or hydrogenated or acetylated lanolin.

Among the oils there may be mentioned inorganic, animal or vegetable oils or synthetic oils, and in particular liquid paraffin, paraffin oil, castor oil, jojoba oil or sesame oil as well as silicone oils and gums and the isoparaffins.

Among the animal, fossil, vegetable, mineral or synthetic waxes there may in particular be mentioned beeswax, carob wax, candelilla wax, ozokerite and microcrystalline waxes as well as silicone waxes and resins.

Among the thickening agents there may be mentioned:

modified celluloses such as hydroxyethyl cellulose, methylcellulose, hydroxypropyl cellulose and carboxymethylcellulose. Among the latter, there may in particular be mentioned the gums sold under the name "Cellosize QP 4400H" by the company Amerchol, carob gum, guar gum, hydroxypropylguar gum and xanthan gum, crosslinked polyacrylic acids such as Carbopols from the Company Goodrich and Synthalen K, L or M from the company Sigma, glyceryl poly(meth)acrylate polymers sold under the names "Hispagel" or "Lubragel" by the companies Hispano Quimica or Guardian, polyvinylpyrrolidone, polyvinyl alcohol, crosslinked polymers of acrylamide and ammonium acrylate sold under the names "PAS 5161" or "Bozepol C" by the company Hoechst, crosslinked polymers of acrylamide and 2-acrylamido-2-methylpropanesulphonic acid, partially or totally neutralized, sold under the name "Sepigel 305" by the company Seppic, crosslinked polymers of acrylamide and methacryloyloxyethyl-trimethylammonium chloride sold under the name "Salcare SC92" by the company Allied Colloids, or alternatively homopolymers or copolymers derived from acrylic acid such as the product sold under the name "Acrysol ICS-1" by the company Seppic, polyurethane latexes such as the product sold under the name "DSX-1514" by the company Henkel.

The thickening agents particularly preferred are those sold under the name "Synthalen K" by the company Sigma, "Acrysol ICS-1" by the company Seppic and "DSX-1514" by the company Henkel.

Several examples of the preparation of the pseudo-latexes and several examples of cosmetic compositions will now be given by way of illustration.

EXAMPLES OF THE PREPARATION OF PSEUDO-LATEXES

Example 1

Preparation of a pseudo-latex of the vinyl acetate/crotonic acid/vinyl 4-tert-butylbenzoate (65/10/25) copolymer neutralized with L-lysine The preparation of this copolymer is described in Example 19 of French Patent No. 78,30596 (2,439,798) and takes the form of beads having a diameter of 0.5 to 1 mm.

44.8 g of tripropylene glycol monomethyl ether and 531.2 g of acetone are successively introduced into a reaction flask.

The mixture is stirred vigorously using a mechanical stirrer and 224 g of the copolymer defined above are slowly introduced. Dissolution occurs rapidly in the closed flask without heating.

When the organic phase is totally solubilized, a disperser of the Ultra Turrax, Moritz or Raineri type is connected to the flask and it is stirred briskly (approximately 2,000 rev/min). An aqueous phase is then introduced in small portions, in order to produce the emulsion, this aqueous phase consisting of 532 g of deionized water and 2.55 g of "Burst RSD 10" silicone-containing anti-foaming agent and 19.033 g of L-lysine (amount corresponding to 50% neutralization according to the acid number of the copolymer).

A decrease in the viscosity is observed during the phase inversion. The aqueous phase is generally added over five minutes and the stirring is continued for 10 to 15 minutes. A translucent and stable emulsion is thus obtained.

The emulsion is then introduced into a round-bottomed flask and then concentrated under vacuum using a rotary evaporator, without exceeding a temperature of 45° C. After complete removal of the acetone, a stable, milky dispersion which is sparingly viscous is obtained, with a film-forming polymer concentration of 27.27%. The viscosity measured on a Contraves machine at 20° C. is $9.5 \times 10^{-3}$ Pa.s (9.5 cP). The size of the particles of the pseudo-latex obtained was measured by quasi-elastic light scattering on a Coulter Model M4 machine and the following results were obtained:

average particle size: 55 nm polydispersity factor: 0.23

Examples 2–3–4

According to the same experimental procedure as described above in Example 1, other pseudo-latexes were also prepared from various film-forming copolymers containing carboxylic acid functions. The production conditions and characteristics of the pseudo-latexes obtained are given in Table I below.

TABLE I

| PSEUDO-LATEX | Example 2 | Example 3 | Example 4 | Example 5 | Example 6 |
| --- | --- | --- | --- | --- | --- |
| Film-forming polymer (AN = acid number) | Resin 28-29-30 AN = 65 | Luviset CA 66 AN = 74 | Amphomer LV71 AN = 137 | idem Ex. 1 AN = 65 | idem Ex. 1 AN = 65 |
| Neutralizing agent | Lysine | Lysine | Lysine | Lysine | Lysine |
| Degree of neutralization | 50% | 50% | 30% | 40% | 40% |

TABLE I-continued

| PSEUDO-LATEX | Example 2 | Example 3 | Example 4 | Example 5 | Example 6 |
|---|---|---|---|---|---|
| ORGANIC PHASE | | | | | |
| Amount of polymer | 75 g | 75 g | 10 g | 100 g | 100 g |
| Tripropylene glycol monomethyl ether | 15 g | 15 g | 2 g | 10 g | 20 g |
| Volatile organic solvent | Methyl ethyl ketone 425 g | Methyl ethyl ketone 300 g | Tetrahydrofuran 38 g | Acetone 290 g | Acetone 280 g |
| AQUEOUS PHASE | | | | | |
| Silicone-containing anti-foaming agent | 0.85 g | 0.85 g | 0.85 g | 1.14 g | 1.14 g |
| Amount of L-lysine | 6.15 g | 7.23 g | 1.07 g | 6.78 g | 6.78 g |
| Deionized water | 230 g | 225 g | 17.7 g | 282 g | 272 g |
| Temperature of formation | 60° C. | Ambient | Ambient | Ambient | Ambient |
| Concentration of the polymer in the pseudo-latex | 23.50% | 20% | 22% | 25% | 25% |
| Average particle size | 254 nm | 240 nm | 423 nm | 71 nm | 69 nm |
| Particle size polydispersity | 0.18 | 0.25 | 0.3 | 0.22 | 0.2 |

Example 7

Preparation of a pseudo-latex of the vinyl acetate/crotonic acid/vinyl 4-tert-butylbenzoate (65/10/25) copolymer neutralized with L-arginine 2.8 g of tripropylene glycol monomethyl ether and 69.2 g of acetone are successively introduced into a reaction flask.

The mixture is stirred vigorously using a mechanical stirrer and 28 g of vinyl acetate/crotonic acid/vinyl 4-tert-butylbenzoate (65/10/25) copolymer used in Example 1 are slowly introduced. Dissolution occurs rapidly in the closed flask without heating.

When the organic phase is totally solubilized, a Moritz disperser is connected to the flask and it is stirred briskly (approximately 2,500 rev/min). An aqueous phase is then introduced in small portions, in order to produce the emulsion, this aqueous phase consisting of 66.05 g of deionized water, 0.32 g of "Burst RSD 10" silicone-containing anti-foaming agent and 2.831 g of L-arginine (amount corresponding to 50% neutralization according to the acid number of the copolymer).

The aqueous phase is generally added over 10 minutes and the stirring is continued for approximately 15 minutes at 3,000 rev/min. A milky emulsion is thus obtained. 180 g of deionized water are then added to this emulsion with stirring.

The emulsion is then introduced into a round-bottomed flask and then concentrated under vacuum using a rotary evaporator.

An aqueous dispersion with a film-forming polymer concentration of 10% is obtained. The size of the particles of the pseudo-latex obtained was measured by quasi-elastic light scattering using a Coulteur Model M4 machine and the following results were obtained:

Average particle size: 38 nm

Polydispersity factor: 0.40

Evaporation of the aqueous dispersion was then continued using a rotary evaporator until a final concentration of film-forming polymer of 27% was obtained.

Example 8

Preparation of a pseudo-latex of the vinyl acetate/crotonic acid/vinyl 4-tert-butylbenzoate (65/10/25) copolymer neutralized with zinc acetate/NaOH (a) 20 g of vinyl acetate/crotinic acid/vinyl 4-tert-butylbenzoate (65/10/25) copolymer used in Example 1 are dissolved in 60 g of acetone and 2.146 g of an aqueous solution containing 10% by weight of zinc acetate dihydrate are then added with stirring. A homogeneous and clear medium is obtained. The amount of zinc acetate corresponds to 4.9% neutralization of the carboxylic groups of the copolymer. 2.9 g of aqueous 4M sodium hydroxide solution, which amount corresponds to neutralization of 50% of the carboxylic groups of the copolymer, are subsequently added to the organic solution.

The organic phase is stirred (approximately 2,000 rev/min) using a Moritz disperser. An aqueous phase is then introduced in small portions, in order to produce the emulsion, this aqueous phase consisting of 60 g of water, 4 g of tripropylene glycol monomethyl ether and 0.2 g of "Burst RSD 10" silicone-containing anti-foaming agent. After production of the emulsion, the acetone is evaporated off as described in Example 1.

A stable dispersion with a film-forming polymer concentration of 22.4% is obtained.

Average particle size: 300 nm

Polydispersity factor: 0.23.

(b) The process is performed in the same way as in Example 8(a) using the following amounts of reagents:

| | |
|---|---|
| Copolymer used in Example 1 | 20 g |
| Acetone | 60 g |
| Aqueous solution containing 10% zinc acetate | 3.28 g (corresponding to 7.5% neutralization of the carboxylic acid functions) |
| Aqueous 4M sodium hydroxide solution | 4.35 g (corresponding to 75% neutralization of the carboxylic acid functions) |
| Aqueous phase identical to that of Example 8(a) | |

A stable dispersion with a film-forming polymer concentration of 21.7% is obtained.

Average particle size: 75 nm

Polydispersity factor: 0.4.

Example 9

Preparation of a pseudo-latex of the vinyl acetate/crotonic acid/vinyl 4-tert-butylbenzoate (65/10/25) copolymer neutralized with zinc acetate/lysine The process is performed in the same way as in Example 8(a) using the following amounts of reagents:

| | |
|---|---|
| Copolymer used in Example 1 | 20 g |
| Acetone | 60 g |
| Aqueous solution containing 10% zinc acetate | 2.146 g (corresponding to 5% neutralization of the carboxylic acid functions) |
| Aqueous solution containing 50% by weight of lysine | 2.4 g (corresponding to 50 g of total neutralization of the carboxylic acid functions) |
| Aqueous phase identical to that of Example 8(a) | |

A stable dispersion with a film-forming polymer concentration of 22% is obtained.

Average particle size: 300 nm

Polydispersity factor: 0.2.

EXAMPLES OF COMPOSITIONS

In the examples which follow, the letters "AS" mean "active substance" when the product used, which may or may not be a commercially available material, is in the form of a solution or a dispersion in a solvent.

Example 1
Mascara cream

| | | |
|---|---|---|
| Phase A: | | |
| Triethanolamine stearate | 11 g | |
| Beeswax | 5 g | |
| Carnauba wax | 3 g | |
| Paraffin | 1 g | |
| Phase B: | | |
| Black iron oxide | 5 g | |
| Phase C: | | |
| Gum arabic | 2 g | |
| Hydroxyethylcellulose sold under the name "Cellosize QP" by the company Amerchol | 1 g | |
| Phase D: | | |
| Pseudo-latex of Example 1 | 6 g (AS) | |
| Preservatives | qs | |
| Water | qs | 100 g |

This mascara is obtained by bringing the ingredients of Phase A to 85° C., to which is added Phase B, and stirring is carried out using a turbine.

The water of the preparation is subsequently boiled and the preservatives are added, followed, at 85° C., by the ingredients of Phase C.

The aqueous phase obtained is then added (85° C.) to Phase A (80° C.) with stirring using a turbine (emulsification) and the pseudo-latex of Phase D is then added, at 30° C., and stirred using a blade.

Example 2
Waterproof mascara

A water-resistant mascara is prepared, having the following composition:

| | |
|---|---|
| Paraffin wax | 12 g |
| Lanolin alcohol | 15 g |
| Starch | 2 g |

-continued

| | |
|---|---|
| Iron oxide | 5 g |
| Isoparaffin | 45 g |
| Montmorillonite | 8 g |
| Pantothenol | 3 g |
| Pseudo-latex of Example 1 | 5 g |
| Preservatives | qs |

This mascara is obtained by mixing the components of the fatty phase and the optional fat-soluble additives. The optional pigments and/or fillers are then added to the mixture thus obtained, followed by the volatile organic solvent (s).

Finally, the aqueous phase of the pseudo-latex and the optional water-soluble active ingredients and/or additives are dispersed in the resulting mixture.

Examples 3 to 7
Nail varnish

| | EXAMPLES | | | | |
|---|---|---|---|---|---|
| | 3 | 4 | 5 | 6 | 7 |
| Pseudo-latex of Example 1 (AS) | 28 g | 28 g | 14 g | 5.6 g | 14 g |
| Tripropylene glycol monomethyl ether | 2.8 g | 1.4 g | 0.7 g | 0.28 g | 0.7 g |
| Acrylic dispersion (1) | — | — | 14 g | 22.4 g | — |
| Polyurethane dispersion (2) | — | — | — | — | 14 g |
| Thickening agent of the polyurethane type (3) | 0.3 g | 0.35 g | 0.3 g | 0.3 g | 0.4 g |
| Anti-foaming agent (4) | 0.5 g | 0.5 g | 0.5 g | 0.5 g | 0.5 g |
| Perfluoroalkyl surfactant (5) | 0.2 g | — | 0.2 g | — | — |
| Dimethicone copolyol butyl ether (6) | — | 0.15 g | — | 0.15 g | 0.15 g |
| Pigments qs | | | | | |
| Water qs | 100 g | 100 g | 100 g | 100 g | 100 g |

(1) sold under the name "Neocryl XK51" by the company ICI,
(2) sold under the name "Neorez R974" by the company ICI,
(3) sold under the name "Rheolate 255" by the company Rheox,
(4) sold under the name "Emulsion SF6" by the company Wacker,
(5) sold under the name "Fluorad FC143" by the company 3M,
(6) sold under the name "KF355A" by the company Shin Etsu.

Experimental Procedure

The pseudo-latex of Example 1, optionally in the presence of the acrylic or polyurethane dispersion, is mixed in a single portion with the thickening agent and the various additives. Stirring is carried out until a homogeneous mixture is obtained and the pigments, which have been ground beforehand in an aqueous medium, are then dispersed therein.

Upon application of the varnish to the nail, a shiny, smooth and hard film is obtained which adheres to the nail.

Example 8
Hair lotion

| | | |
|---|---|---|
| Pseudo-latex of Example 1 | | 20 g (AS) |
| Perfume, dye, preservative | qs | |
| Demineralized water | qs | 100 g |

On application to hair, this lotion gives excellent hold to the hair, even after shampooing three times.

Example 9
Styling gel

| | | |
|---|---|---|
| Pseudo-latex of Example 2 | | 10 g (AS) |
| Crosslinked polyacrylic acid sold under the name "Carbopol 980" by the company Goodrich | | 0.3 g |
| Perfume, dye, preservative | qs | |
| Demineralized water | qs | 100 g |

On application to hair, this gel gives a measure of softness, even after shampooing three times.

Example 10
Water-in-oil suncare emulsion

| | | |
|---|---|---|
| Mixture of cetyl-stearyl alcohol and oxyethylenated cetyl-stearyl alcohol containing 33 moles of ethylene oxide, sold under the name "Synnowax AO" by the company Henkel | | 7 g |
| Non-automemulsifiable mixture of glyceryl monostearate and distearate | | 2 g |
| Cetyl alcohol | | 1.5 g |
| Silicone oil | | 1.5 g |
| Liquid paraffin | | 15 g |
| Camphorsulphonic acid in aqueous solution at a concentration of 35% | | 3 g (AS) |
| Triethanolamine | | 1.8 g |
| Pseudo-latex of Example 1 | | 5 g (AS) |
| Glycerine | | 20 g |
| Perfume, preservatives | qs | |
| Water | qs | 100 g |

Example 11
Shampoo

| | | |
|---|---|---|
| Alkyl ($C_9/C_{10}/C_{11}$, 20/40/40) (1 → 4)-polyglycoside at a concentration of 50% sold under the name "APG 300" by the company Henkel | | 15 g (AS) |
| Pseudo-latex of Example 1 | | 3 g (AS) |
| HCl | qs pH6 | |
| Preservative, perfume | qs | |
| Water | qs | 100 g |

Example 12
Shampoo

| | | |
|---|---|---|
| Neutralized oxyethylenated lauryl ($C_{12}/C_{14}$, 70/30) ether carboxylic acid containing 4.5 moles of ethylene oxide, sold under the name "Akypo RLM 45" by the company Chem. Y | | 8 g (AS) |
| Sodium N-cocoamidoethyl-N-ethoxycarboxymethylglycinate | | 4 g |
| Pseudo-latex of Example 5 | | 3 g (AS) |
| HCl | qs pH7 | |
| Preservative, perfume | qs | |
| Water | qs | 100 g |

Example 13
Styling lotion

| | | |
|---|---|---|
| Acrylamide/Acid acrylamido-2-methylpropanesulphonic copolymer in the form of the sodium salt as an inverted emulsion at a concentration of 40% in isoparaffin/water sold under the name "Sepigel 305" by the company Seppic | | 1 g (AS) |
| Pseudo-latex of Example 1 | | 3 g (AS) |
| NaOH | qs pH 7.5 | |
| Preservative, perfume | qs | |
| Water | qs | 100 g |

Example 14
Lotion presented in a pump-action spray bottle

| | | |
|---|---|---|
| Pseudo-latex of Example 4 | | 8 g (AS) |
| Perfume | qs | |
| Dye | qs | |
| Preservative | qs | |
| Demineralized water | qs | 100 g |

Example 15
Lotion for styling

| | | |
|---|---|---|
| Pseudo-latex of Example 2 | | 10 g (AS) |
| Perfume | qs | |
| Dye | qs | |
| Preservative | qs | |
| Demineralized water | qs | 100 g |

Example 16
Mouthwash

| | | |
|---|---|---|
| Pseudo-latex of Example 1 | | 2.5 g (AS) |
| Sodium fluoride | | 0.04 g |
| Sorbitol (70% in water) | | 8 g |
| Ethyl alcohol | | 6 g |
| Polyoxyethylenated hydrogenated castor oil containing 40 moles of ethylene oxide, sold under the name "Cremophor RH 40" by the company BASF | | 2 g |
| Sodium saccharinate | | 0.015 g |
| Flavouring | qs | |
| Water | qs | 100 g |

Example 17
Deodorant spray

| | | |
|---|---|---|
| Pseudo-latex of Example 1 | | 5 g (AS) |
| 2,2,4'-trichloro-2'-hydroxydiphenyl ether sold under the name "Irgasan DP 300" by the company Ciba Geigy | | 0.3 g |
| Ethyl alcohol | | 40 g |
| Perfume | qs | |
| Water | qs | 100 g |

This composition is packaged in a pump-action bottle for spraying.

Example 18
Hair gel

| | |
|---|---|
| Pseudo-latex of Example 1 | 5 g (AS) |
| Acrylates/steareth-20 methacrylate copolymer sold under the name "Acrysol ICS" by the company | 2 g (AS) |

Example 19
Hair gel

| | |
|---|---|
| Pseudo-latex of Example 5 | 8 g (AS) |
| Crosslinked polyacrylic acid sold under the name "Synthalen K" by the company Sigma | 1 g (AS) |
| Perfume, dye, preservative | qs |
| Water | qs 100 g |

Example 20
Hair gel

| | |
|---|---|
| Pseudo-latex of Example 6 | 3 g (AS) |
| Polyurethane latex sold under the name "DSX 1514" by the company Henkel | 2 g (AS) |
| Perfume, dye, preservative | qs |
| Water | qs 100 g |

Example 21
Hair gel

| | |
|---|---|
| Pseudo-latex of Example 4 | 10 g (AS) |
| Polyurethane latex sold under the name "DSX 1514" by the company Henkel | 2 g (AS) |
| Perfume, dye, preservative | qs |
| Water | qs 100 g |

Example 22
Lotion for styling

| | |
|---|---|
| Pseudo-latex of Example 8(a) | 10 g (AS) |
| Perfume, dye, preservative | qs |
| Demineralized water | qs 100 g |

Example 23
Lotion for styling

| | |
|---|---|
| Pseudo-latex of Example 8(b) | 8 g (AS) |
| Perfume, dye, preservative | qs |
| Demineralized water | qs 100 g |

Example 24
Mascara

According to the same experimental procedure as in Example 1, a mascara is prepared having the following composition:

| | |
|---|---|
| Phase A: | |
| Triethanolamine stearate | 11.8 g |
| Beeswax | 5 g |
| Carnauba wax | 3 g |
| Paraffin | 1 g |
| Phase B: | |
| Black iron oxide | 5 g |
| Phase C: | |
| Gum arabic | 2 g |
| Hydroxyethyl cellulose sold under the name "Cellosize QP" by the company Amerchol | 1.2 g |
| Phase D: | |
| Pseudo-latex of Example 6 | 5 g (AS) |
| Preservatives | qs |
| Water | qs 100 g |

Example 25
Mascara

According to the same experimental procedure as in Example 1, a mascara is prepared having the following composition:

| | |
|---|---|
| Phase A: | |
| Triethanolamine stearate | 12 g |
| Beeswax | 8 g |
| Carnauba wax | 3 g |
| Paraffin | 2 g |
| Phase B: | |
| Black iron oxide | 5 g |
| Phase C: | |
| Gum arabic | 2.5 g |
| Hydroxyethyl cellulose sold under the name "Cellosize QP" by the company Amerchol | 1.5 g |
| Hydrolysate of keratin sold under the name "Kerasol" by the company Croda | 1 g |
| Phase D: | |
| Pseudo-latex of Example 5 | 4 g (AS) |
| Preservatives | qs |
| Water | qs 100 g |

Example 26
Mascara

According to the same experimental procedure as in Example 1, a mascara is prepared having the following composition:

| | |
|---|---|
| Phase A: | |
| Triethanolamine stearate | 11 g |
| Beeswax | 10 g |
| Carnauba wax | 2 g |
| Paraffin | 1 g |
| Phase B: | |
| Black iron oxide | 6 g |
| Phase C: | |
| Gum arabic | 0.8 g |
| Hydroxyethyl cellulose sold under the name "Cellosize QP" by the company Amerchol | 2 g |
| Hydroxyethyl cellulose crosslinked with epichlorohydrin and quaternized with trimethylamine, sold under the name "Celquat SC 240" by the company National Starch | 0.1 g |
| Sodium polymethacrylate sold under the name "Darvan 7" by the company Vanderbilt | 1 g |

Example 27

Mascara

According to the same experimental procedure as in Example 1, a mascara is prepared having the following composition:

Phase A:

| | |
|---|---|
| Glycerol stearate | 3 g |
| Mixture of sorbitol laurate and oxyethylenated sorbitol laurate containing 20 moles of ethylene oxide, sold under the name "Tween 20" by the company ICI | 3.7 g |
| Monoesters of stearic and sorbitan sold under the name "Span 60" by the company ICI | 5.6 g |
| Beeswax | 6 g |
| Carnauba wax | 1.8 g |
| Paraffin | 7.8 g |

Phase B:

| | |
|---|---|
| Black iron oxide | 4.5 g |

Phase C:

| | |
|---|---|
| Hydroxyethyl cellulose sold under the name "Cellosize QP" by the company Amerchol | 1.5 g |

Phase D:

| | | |
|---|---|---|
| Pseudo-latex of Example 3 | | 2 g (AS) |
| Preservatives | qs | |
| Water | qs | 100 g |

Example 28

Mascara

According to the same experimental procedure as in Example 1, a mascara is prepared having the following composition:

Phase A:

| | |
|---|---|
| Triethanolamine stearate | 11 g |
| Beeswax | 5 g |
| Carnauba wax | 3 g |
| Paraffin | 1 g |

Phase B:

| | |
|---|---|
| Black iron oxide | 5 g |

Phase C:

| | | |
|---|---|---|
| Gum arabic | | 2 g |
| Hydroxyethyl cellulose sold under the name "Cellosize QP" by the company Amerchol | | 1 g |

Phase D:

| | | |
|---|---|---|
| Pseudo-latex of Example 7 | | 6 g (AS) |
| Preservatives | qs | |
| Water | qs | 100 g |

Example 29

Lotion for styling

| | | |
|---|---|---|
| Pseudo-latex of Example 8 | | 9 g (AS) |
| Perfume, dye, preservative | qs | |
| Demineralized water | qs | 100 g |

We claim:

1. A cosmetic composition which contains, in suspension in a suitable aqueous cosmetic vehicle, spherical particles of a film-forming radical polymer having carboxylic acid functions neutralized between 10 and 80% by a polyfunctional neutralizing agent selected from the group consisting of a diamine and a combination of a polyvalent metal salt with an inorganic or organic base, wherein said spherical particles have an average diameter of between 10 and 450nm and said composition forms a film that has remanence properties to water and shampoo.

2. Cosmetic composition according to claim 1, wherein the film-forming radical polymer containing carboxylic acid functions has an average molecular weight between 1,000 and $10^6$.

3. Cosmetic composition according to claim 1, wherein the film-forming radical polymer containing carboxylic acid functions is selected from the group consisting of:

polyoxyethylenated vinyl acetate/crotonic acid copolymers, vinyl acetate/crotonic acid (90/10) copolymer, vinyl acetate/crotonic acid/vinyl neodecanoate terpolymers, N-octylacrylamide/methyl methacrylate/hydroxypropyl methacrylate/acrylic acid/tert-butylaminoethyl methacrylate copolymers, alternating methyl vinyl ether/maleic anhydride (50/50) copolymer monoesterified with butanol, and acrylic acid/ethyl acrylate/N-tert-butylacryl-amide terpolymers.

4. Cosmetic composition according to claim 1, wherein the radical polymer containing carboxylic acid functions corresponds to the following formula:

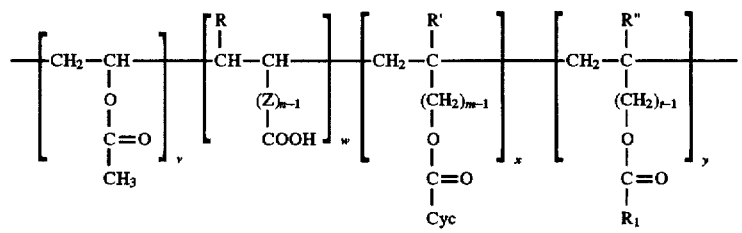

in which

R, R' and R", identical or different, represent a hydrogen atom or a methyl radical, m, n and t are 1 or 2, $R_1$ represents a saturated or unsaturated linear or branched alkyl radical having from 2 to 21 carbon atoms, Z represents a divalent radical selected from the group consisting of: —$CH_2$—, —$CH_2$—O—$CH_2$— and —$CH_2$—O—$(CH_2)_2$—, and Cyc represents a radical selected from the group consisting of:

(i) a radical of formula:

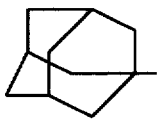

(ii) a radical of formula:

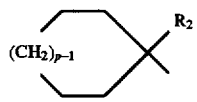

in which:

$R_2$ represents a hydrogen atom or a methyl radical, and p is 1 or 2, (iii) a radical of formula:

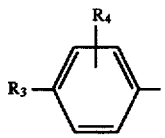

in which:

$R_3$ represents a hydrogen atom, a methyl, ethyl, tertbutyl, ethoxy, butoxy or dodecyloxy radical and $R_4$ represents a hydrogen atom, an alkyl radical of 1 to 4 carbon atoms or an alkoxy radical of 1 to 4 carbon atoms, and (iv) a radical of formula:

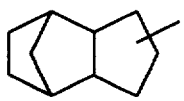

v represents from 10 to 91% by weight, w represents from 3 to 20% by weight, x represents from 4 to 60% by weight, and y represents from 0 to 40% by weight, v+w+x+y being equal to 100%.

5. Cosmetic composition according to claim 1, wherein the film-forming radical polymer containing carboxylic acid functions is neutralized using a diamine selected from the group consisting of lysine, arginine and cystine.

6. Cosmetic composition according to claim 5, wherein if the carboxylic acid functions of the film-forming polymer have less than 2 meq/g of carboxylic acid functions, the degree of neutralization, using the diamine, is between 30 and 80%.

7. Cosmetic composition according to claim 5, wherein the carboxylic acid functions of the film-forming polymer have more than 2 meq/g of carboxylic acid and the degree of neutralization, using the diamine, is between 10 and 50%.

8. Cosmetic composition according to claim 1, wherein the film-forming radical polymer containing carboxylic acid functions is neutralized using a combination of a polyvalent metal salt and an inorganic or organic base, and the polyvalent metal salt is selected from the group consisting of bromides, chlorides, nitrates, acetates, carbonates and sulphates of at least one member selected from the group consisting of calcium, zinc, magnesium, barium, aluminum and zirconium, and the inorganic or organic base is selected from the group consisting of sodium hydroxide, potassium hydroxide, aqueous ammonia, an amino alcohol selected from the group consisting of 2-amino-2-methyl-1-propanol (AMP), triethanolamine, triisopropanolamine (TIPA), monoethanolamine, diethanolamine, tri[1-(2-hydroxy) propyl]amine, 2-amino-2-methyl-1,3-propanediol (AMPD) and 2-amino-2-hydroxymethyl-1,3-propanediol, and a diamine.

9. Cosmetic composition according to claim 8, wherein the carboxylic acid functions of the film-forming polymer have less than 2 meq/g of carboxylic acid and the polymer is neutralized with the polyvalent metal salt to a degree between 4 and 20%, and co-neutralized with the inorganic or organic base to a total degree of neutralization between 30 and 80%.

10. Cosmetic composition according to claim 8, wherein the carboxylic acid functions of the film-forming polymer have more than 2 meq/g of carboxylic acid and, the polymer is neutralized with the polyvalent metal salt to a degree between 4 and 20%, and co-neutralized with the inorganic or organic base to a total degree of neutralization between 10 and 50%.

11. Cosmetic composition according to claim 1, wherein said composition contains from 0.5 to 30% by weight of particles of the film-forming polymer relative to the total weight of the composition.

12. Cosmetic composition according to claim 1, wherein the pseudo-latex contains a plasticizing agent in a proportion between 5 and 40% by weight relative to the film-forming polymer.

13. Composition according to claim 1, wherein said composition further contains at least one cosmetic additive selected from the group consisting of: a fatty substance, an organic solvent, a silicone, a thickening agent, an emollient, a UV-A or UV-B or broad-band sunscreen agent, an anti-forming agent, a moisturizing agent, a humidifying agent, an anionic, non-ionic or amphoteric polymer or a mixture thereof, an anti-perspirant, a basifying agent, a dye, a pigment and a propellent.

14. Composition according to claim 1, wherein said composition contains a thickening agent selected from the group consisting of modified celluloses, carob gum, guar gum, hydroxypropylguar gum, xanthan gum, crosslinked polyacrylic acids, glyceryl poly(meth)acrylate polymers, polyvinylpyrrolidone, polyvinyl alcohol, crosslinked polymers of acrylamide and ammonium acrylate, crosslinked polymers of acrylamide and 2-acrylamido-2-methylpropanesulphonic acid, crosslinked polymers of acrylamide and methacryloyloxyethyltrimethylammonium chloride, homopolymers or copolymers derived from acrylic acid and polyurethane latexes.

15. The cosmetic composition of claim , wherein in the formula:

v represents from 36 to 84% by weight, w represents from 6 to 12% by weight, x represents from 6 to 40% by weight, and y represents from 4 to 30% by weight, v+w+x+y being equal to 100%.

16. The cosmetic composition according to claim 1, wherein said spherical particles are present in an amount of from 0.5 to 30% by weight relative to the total weight of the composition.

* * * * *

UNITED STATES PATENT AND TRADEMARK OFFICE
CERTIFICATE OF CORRECTION

PATENT NO. : 5,753,215
DATED : May 19, 1998
INVENTOR(S) : Nathalie Mougin, Jean Mondet, Monique Guelton, Bertrand Piot, Christine Dupuis and Daniele Cauwet It is certified that error appears in the above-indentified patent and that said Letters Patent is hereby corrected as shown below:

Column 13, line 14, change "Water-in-oil" to --Oil-in-water--.

Signed and Sealed this

Third Day of April, 2001

Attest:

NICHOLAS P. GODICI

Attesting Officer    Acting Director of the United States Patent and Trademark Office